(12) United States Patent
Lucas et al.

(10) Patent No.: US 11,357,638 B2
(45) Date of Patent: Jun. 14, 2022

(54) PROSTHETIC ANKLE WITH A FLAT SECTION

(71) Applicant: I.CERAM, Limoges (FR)

(72) Inventors: Julien Lucas, Merignac (FR); Eric Toullec, Tournefeuille (FR)

(73) Assignee: I.CERAM, Limoges (FR)

( * ) Notice: Subject to any disclaimer, the term of this patent is extended or adjusted under 35 U.S.C. 154(b) by 0 days.

(21) Appl. No.: 17/055,697

(22) PCT Filed: May 14, 2019

(86) PCT No.: PCT/FR2019/051084
§ 371 (c)(1),
(2) Date: Nov. 16, 2020

(87) PCT Pub. No.: WO2019/220048
PCT Pub. Date: Nov. 21, 2019

(65) Prior Publication Data
US 2021/0186705 A1 Jun. 24, 2021

(30) Foreign Application Priority Data

May 17, 2018 (FR) ...................................... 1854122

(51) Int. Cl.
*A61F 2/42* (2006.01)
*A61F 2/30* (2006.01)
(52) U.S. Cl.
CPC .. *A61F 2/4202* (2013.01); *A61F 2002/30158* (2013.01); *A61F 2002/30242* (2013.01); *A61F 2002/30878* (2013.01); *A61F 2002/30934* (2013.01); *A61F 2002/4205* (2013.01); *A61F 2002/4207* (2013.01)

(58) Field of Classification Search
CPC ............ A61F 2/4202; A61F 2002/4205; A61F 2002/4207
See application file for complete search history.

(56) References Cited

U.S. PATENT DOCUMENTS

| 7,323,012 B1 | 1/2008 | Stone et al. |
| 2006/0142870 A1 | 6/2006 | Robinson et al. |
| 2013/0090739 A1 | 4/2013 | Linares et al. |

FOREIGN PATENT DOCUMENTS

| FR | 2 760 353 A1 | 9/1998 |
| FR | 2 905 259 A1 | 3/2008 |
| WO | WO 03/075802 A1 | 9/2003 |

OTHER PUBLICATIONS

English Translation of FR 2905259 A1 (included in IDS) (Year: 2008).*
International Search Report, issued in PCT/FR2019/051084, dated Jul. 24, 2019.

* cited by examiner

*Primary Examiner* — Brian A Dukert
(74) *Attorney, Agent, or Firm* — Birch, Stewart, Kolasch & Birch, LLP

(57) ABSTRACT

A prosthetic ankle includes a tibial portion likely to be connected to the lower end of a tibia, a talus portion likely to be connected to a talus, and a pad inserted between the tibial portion and the talus portion. The tibial portion includes an articular surface likely to engage with a contact surface of the pad. The talus portion includes a curved articular surface likely to engage with a contact surface of the pad. The articular surface of the tibial portion is curved, concave and includes a flat section forming an extension to the rear of said articular surface.

14 Claims, 4 Drawing Sheets

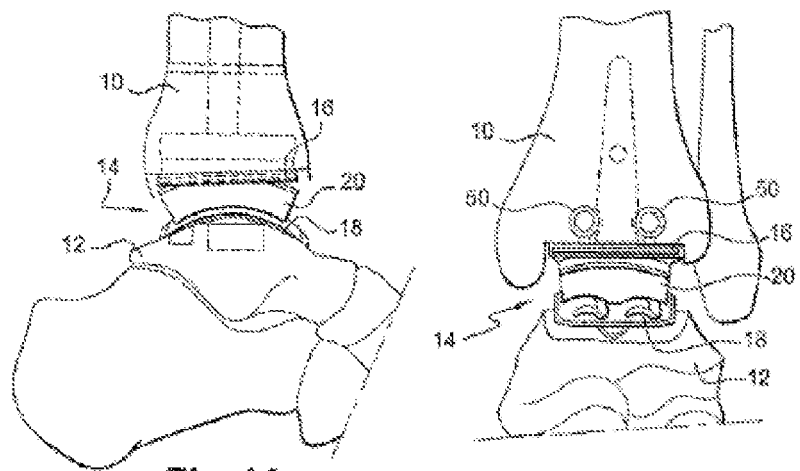
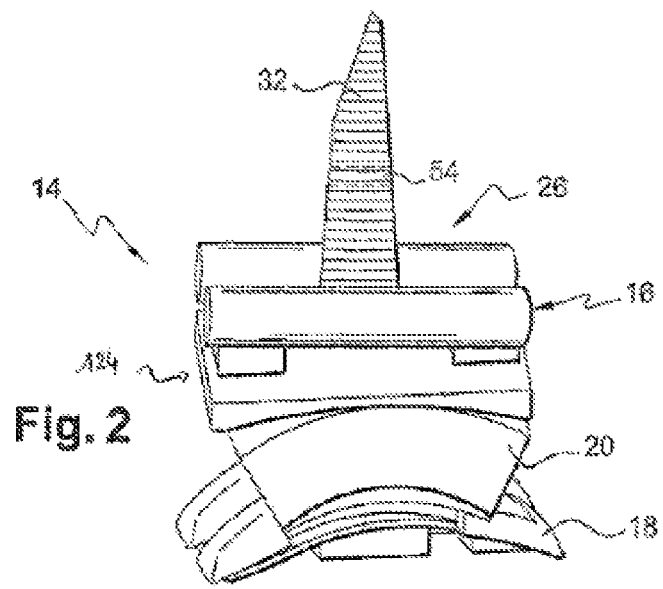

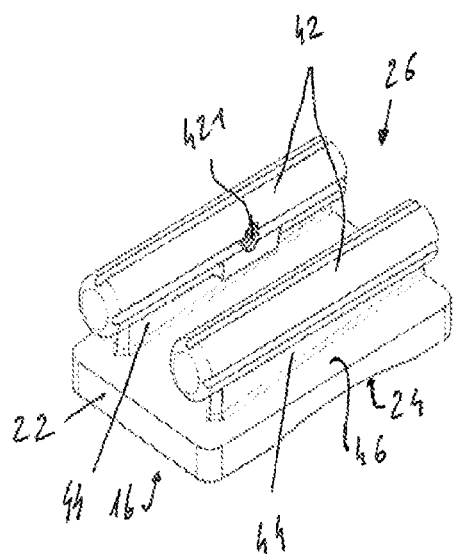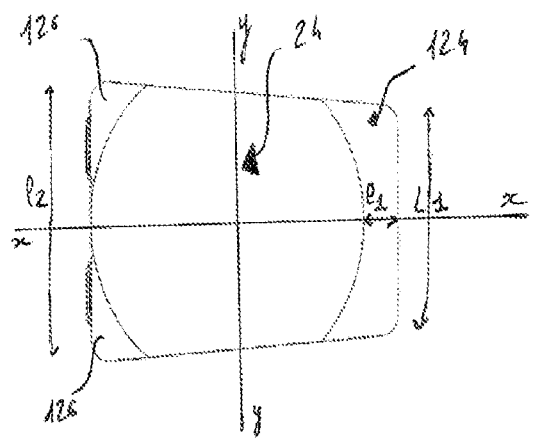
Fig.16    Fig.17
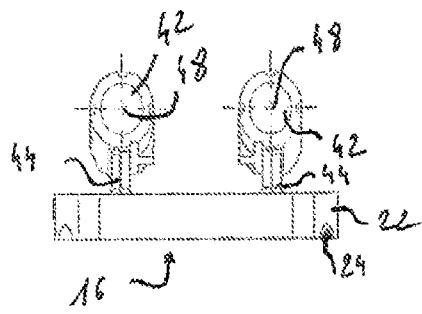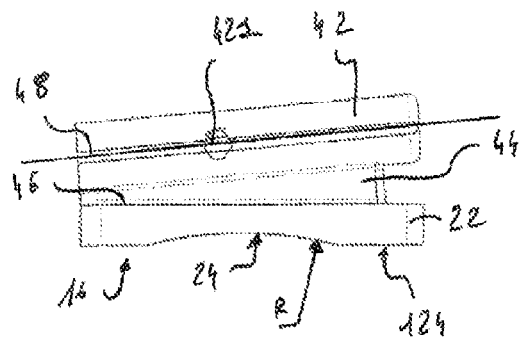
Fig.18    Fig.19

PROSTHETIC ANKLE WITH A FLAT SECTION

FIELD OF THE INVENTION

The present invention relates to a prosthetic ankle including a flat section.

TECHNICAL BACKGROUND

The present invention relates to the technical field of prosthetic ankles intended to allow for an orthopaedic treatment of the articulation of the ankle by implantation of prosthetic elements to return at least partially the articular anatomy of the ankle. Indeed, following wear or a traumatic shock, it is known that total or partial damage of the articular interlining of the ankle occurs.

Numerous prosthetic ankles have been developed.

They generally comprise two portions; a tibial portion provided at the end of the tibia, a talus portion provided in the upper portion of the talus, each of the two portions including an articular surface, as well as a pad inserted between the tibial portion and the talus portion with two contact surfaces likely to supplement the articular surfaces. For example, such prosthetic ankles are described in the documents FR 2 760 353 and WO 03/075802.

Document FR 2 905 259 describes a prosthetic ankle comprising a talus portion, a pad and a tibial portion having a curved, concave articular surface constituted of a spheric portion extending over all of said articular surface.

These stressed systems only make it possible to reproduce partially all of the freedoms of movements of the natural articulation of the ankle since the friction surface between the two implants is very distant from the theoretical physiological shape of the natural articulation of the ankle.

There is therefore a real need to propose a prosthetic ankle, of which the shapes make it possible to improve the freedom of movements while allowing for a correct centring of stresses and to reduce the stresses, in particular at the level of the anchorages, and to improve said anchorages, in particular in order to obtain a better bone recovery and to improve the articular amplitudes in a front plane.

SUMMARY OF THE INVENTION

The invention first relates to a prosthetic ankle comprising a tibial portion likely to be connected to the lower end of a tibia, a talus portion likely to be connected to a talus, as well as a pad inserted between the tibial portion and the talus portion, the tibial portion including an articular surface likely to engage with a contact surface of the pad and the talus portion including a curved articular surface likely to engage with a contact surface of the pad, characterised in that the articular surface of the tibial portion is curved, concave, and comprises a flat section forming an extension to the rear of said articular surface.

According to an embodiment, the flat section has a width comprised between 2 and 8 mm, preferably between 4 and 6 mm.

According to an embodiment, the tibial portion has a length comprised between 20 and 100 mm, preferably between 35 and 85 mm and a width comprised between 10 and 40 mm, preferably between 15 and 30 mm.

According to an embodiment, the articular surface of the tibial portion comprises a spheric portion extending over a portion of said articular surface.

According to an embodiment, the spheric portion of the articular surface of the tibial portion has a bend radius R likely to vary from 30 to 90 mm, preferably of the order of 50 mm, and if necessary, a second bend radius R' different from the radius R likely to vary from 20 to 80 mm, preferably of the order of 50 mm.

According to an embodiment, the articular surface of the tibial portion is slightly inclined to the rear of the foot.

According to an embodiment, the articular surface of the tibial portion is inclined in the direction of the flat section.

According to an embodiment, the articular surface of the tibial portion is inclined in the direction of the rear portion of the articular surface.

According to an embodiment, the articular surface of the talus portion has a bend radius r about the longitudinal axis likely to vary from 20 to 30 mm, preferably of the order of 24 mm.

According to an embodiment, the tibial portion comprises anchorage means with a removable pin.

According to an embodiment, the removable pin comprises two symmetrical recesses arranged in the lower portion of the pin, of which the shapes are likely to engage with the outer surfaces of two parallel cylinders integral with tibial portion, the pin having in the lower portion, a diameter greater than the distance separating the two cylinders.

According to an embodiment, the pin comprises a transversal orifice allowing for the implementation of a screw, a cotter or a linchpin likely to pass through at least partially the lower portion of the tibia.

According to an embodiment, the talus portion comprises anchorage means with at least one stop arranged under the talus portion, at the level of the rear edge, to prevent the tilting of the talus portion towards the front of the foot.

The present invention makes it possible to overcome the disadvantages of the state of the art.

To this end, the invention aims for a prosthetic ankle comprising a tibial portion likely to be connected to the lower end of a tibia, a talus portion likely to be connected to a talus, as well as a pad inserted between the tibial portion and the talus portion, the tibial portion including an articular surface likely to engage with a contact surface of the pad and the talus portion including a curved articular surface likely to engage with a contact surface of the pad, characterised in that the articular surface of the tibial portion is curved, concave, and further comprises a flat section forming an extension to the rear of said articular surface of the tibial portion.

BRIEF DESCRIPTION OF THE FIGURES

Other features and advantages will emerge from the following description of the invention, given only as an example, regarding the appended drawings, wherein:

FIG. 1A is a side view of an ankle equipped with a prosthetic ankle according to the invention, FIG. 1B is a front view of the ankle represented in FIG. 1A, FIG. 2 is a perspective view of a prosthetic ankle according to the invention, FIG. 16 is a perspective view of the tibial portion of the prosthetic according to an embodiment of the invention, FIG. 17 is a top view illustrating the articular surface of the tibial portion according to an embodiment of the invention, FIG. 18 is a side view along a first direction of the tibial portion according to an embodiment of the invention, and FIG. 19 is a side view along another direction of the tibial portion according to an embodiment of the invention.

DESCRIPTION OF EMBODIMENTS OF THE INVENTION

Figure 3A:
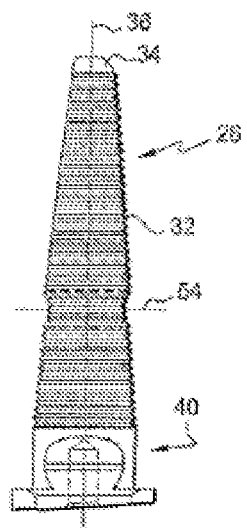
FIG. 3A is a side view of a removable pin according to the invention.

In FIGS. 1A and 1B, an ankle has been represented with, in 10, the lower portion of a tibia and, in 12, a talus, said ankle being equipped of a prosthetic ankle 14.

As illustrated in FIG. 2, the prosthetic ankle comprises a tibial portion 16 connected to the lower end of the tibia 10 (not represented in FIG. 2), a talus portion 18 connected to the talus 12 (not represented in FIG. 2), as well as a pad 20 inserted between the tibial portion 16 and the talus portion 18.

In FIGS. 4 to 7 and 16 to 19, in detail, the tibial portion 16 has been represented. It comprises a body 22 in the shape of a plate with, on one side, a curved, concave articular surface 24, having a flat section 124, and on the other side, means 26 for anchoring the tibia 10.

According to an important feature of the invention, the articular surface 24 is not flat, but curved.

According to an embodiment, the articular surface 24 comprises a sphere portion. The sphere can be an equal radius or the spheric portion can be slightly deformed. Through that, it is understood that the bend radiuses R and R' can observe slight variations along the axes x/x and y/y.

Thus, according to an embodiment, the sphere portion can be a radius R varying from 30 to 90 mm, preferably of the order of 50 mm.

According to an embodiment, the articular surface 24 comprises a second bend radius R' (slightly different from R to form a slightly deformed sphere), varying for example from 20 to 80 mm, preferably of the order of 50 mm.

According to this embodiment, the articular surface 24 thus adopts a substantially spheric shape with bend radiuses R and R', the bend radius R being situated along an axis x/x (axis defined by the front and the rear of the foot) and the bend radius R' being situated along an axis y/y (y/y is perpendicular to x/x and y is an axis defined by the right and the left of the foot). Preferably, the ratio R/R' is greater than 1, preferably even greater than 1.2. The bend radius along the axis x/x is generally greater than the bend radius along the axis y/y. The bend radius along the axis x/x is the bend radius which supports the pad 20 in its movements (from the front to the rear of the foot). This configuration allows for a better distribution of the contact pressures and a better transmission of the forces between the pad 20 and the tibial portion 16, which tends to reduce the stresses at the level of the anchorage.

According to an embodiment, the centre of the sphere defined by the radius(es) R and/or R' is arranged on an axis 28 slightly inclined in the longitudinal vertical plane of the foot, the centre being offset towards the front of the foot.

According to the invention, the articular surface 24 has a flat section 124 situated forming an extension to the rear of the articular surface 24. By "extension to the rear" of the articular surface 24, this means the portion of the articular surface 24 directed towards the talon, towards the rear of the foot. This configuration makes it possible to avoid a modification of the axis of anatomic rotation during the movement of the patient, thanks to a perfect distribution of the stresses on the cortical tibial bone. A decrease of the stress peak on the pad 20 is also observed. Thus, a perfect rear tibial coverage is observed.

According to an embodiment, the articular surface 24 has at least one flat section 124 situated forming an extension to the rear of the articular surface 24 such that the centre of the sphere defined by the radius(es) R and/or R' is not in the centre of the tibial portion 16 along the antero-posterior axis. Thus, the centre of the sphere defined by the radius(es) R and/or R' is situated in the front portion of the tibial portion. It is offset in the opposite direction to the flat section (i.e. towards the front along the antero-posterior axis x/x). In this way, the centre of the sphere is closer to the centre of anatomic rotation.

According to an embodiment, the flat section 124 is sized such that the centre of the sphere defined by the radius(es) R and/or R' is offset to the front of the centre of the tibial portion 16 along the antero-posterior axis x/x of 5 to 30%, preferably 10 to 20%, with respect to the total dimension of the tibial portion 16.

According to an embodiment, the articular surface 24 has one single flat section 124 situated forming an extension to the rear of the articular surface. Thus, the centre of the sphere defined by the radius(es) R and/or R' is offset in the direction opposite the flat section.

According to an embodiment, the flat section is continuous from one edge to the other of the tibial portion. Thus, FIG. 16 presents a flat section 124 situated forming an extension to the rear of the articular surface 24. This flat section is continuous along the axis y/y. However, FIG. 16 does not present any flat section forming an extension to the rear; the portions 126 not being connected.

According to an embodiment, the flat section 124 has a width I1 comprised between 2 and 8 mm, preferably between 4 and 6 mm (I1 being measured at the centre of the flat section) and a length L1 comprised between 10 and 35 mm, preferably between 15 and 25 mm.

Figure 5:
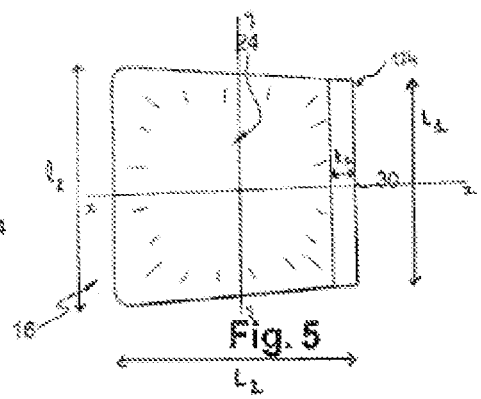
FIG. 5 is a view illustrating the articular surface of the tibial portion according to an embodiment of the invention.
Figure 6:
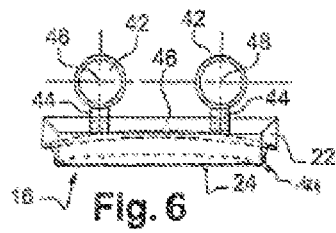
FIG. 6 is a side view along a first direction of the tibial portion according to an embodiment of the invention.
Figure 7:
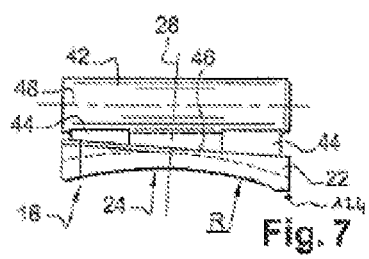
FIG. 7 is a side view along another direction of the tibial portion according to an embodiment of the invention.
Figure 8:
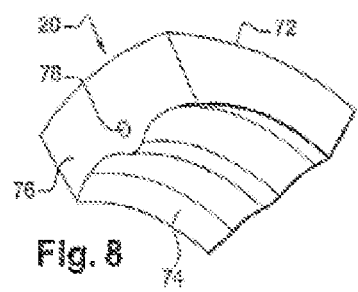
FIG. 8 is a perspective view of the pad of the prosthetic ankle according to the invention.
Figure 9:
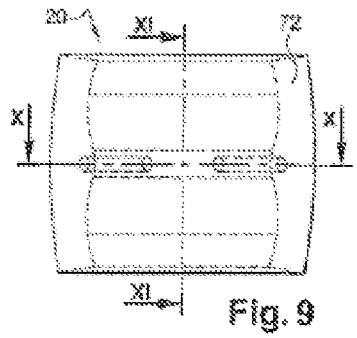
FIG. 9 is a top view of the pad represented in FIG. 8.
Figure 10:
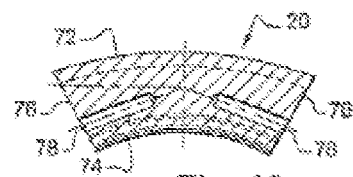
FIG. 10 is a cross-section of the pad along the line X-X of FIG. 9.
Figure 11:
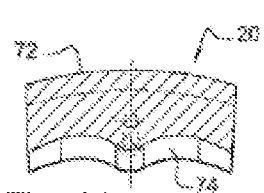
FIG. 11 is a cross-section of the pad along the line XI-XI of FIG. 9.
Figure 12:
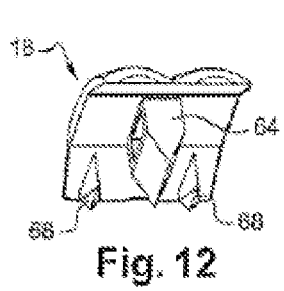
FIG. 12 is a perspective view of the talus portion of the prosthetic ankle according to the invention.
Figure 13:
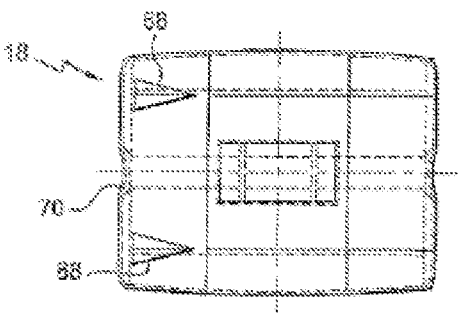
FIG. 13 is a bottom view of the talus portion represented in FIG. 12.

Preferably, the body 22 has a trapezium shape, as illustrated in FIG. 5, the small base 30 being directed towards the talon. This arrangement facilitates the implementation of the tibial portion 16 which is introduced from the front of the ankle. According to this embodiment, the flat section 124 is situated preferably at the level of the small base 30 of the trapezium-shaped body.

According to an embodiment, the tibial portion 16 of the prosthetic ankle has a length L2 comprised between 30 and 100 mm, preferably between 35 and 85 mm and a width I2 comprised between 10 and 40 mm, preferably between 15 and 30 mm.

Figure 3B:
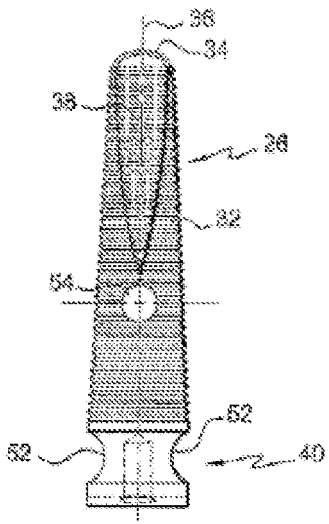
FIG. 3B is a front view of the removable pin represented in FIG. 3A.
Figure 4:
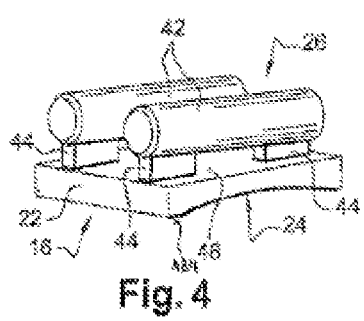
FIG. 4 is a perspective view of the tibial portion of the prosthetic according to an embodiment of the invention.

According to another feature of the invention, means 26 for anchoring the tibial portion comprise a removable pin 32. This feature makes it possible to reduce the manufacturing costs. Indeed, from a limited number of pins and a limited number of tibial portions, it is possible to obtain a large number of combinations likely to correspond to the majority of patients. The removable pin 32 is illustrated in detail in FIGS. 3A and 3B. It comprises a truncated body with a rounded distal end 34. According to the embodiments, the axis 36 of the truncated body can be rectilinear or curved according to the anatomy of the patient. To ensure a better fixing, the body of the pin comprises grooves at the periphery. In addition, as the case may be, the distal portion can comprise a flat section 38.

In the lower portion, the removable pin 32 comprises means 40 for connecting with the tibial portion 16.

The anchorage means 26 can also comprise two cylinders 42 connected by tabs 44 to the body 22 of the tibial portion at the level of the rear surface 46, opposite the articular surface 24. In the embodiment illustrated in FIGS. 4 to 7, each cylinder 42 is connected to the body 22 by way of two tabs 44. In the embodiment illustrated in FIGS. 16 to 19, each cylinder is connected to the body 22 by way of one single tab. In the latter embodiment, at least one of the cylinders 42 comprises a bore 421. These two cylinders 42 have substantially parallel axes 48 which extend along the longitudinal direction of the foot. These two cylinders 42 are slightly offset with respect to the rear surface 46 and are likely to be housed in substantially tubular tunnels or conduits 50 arranged in the lower portion of the tibia 10, as illustrated in FIG. 1B. This arrangement contributes to obtaining a solid anchorage by limiting the use of cement.

Preferably, the axes 48 are not parallel to the rear surface 46 of the tibial portion and form an angle of a few degrees, preferably comprised between 2 and 10°, even more preferably of the order of 4°. This arrangement makes it possible to obtain an articular surface 24 slightly inclined towards the rear of the foot, which contributes to improving the rotational movement of the foot in the longitudinal vertical plane.

According to an embodiment, the means 40 for connecting the removable pin 32 to the tibial portion 16 comprise two symmetrical recesses 52 arranged in the lower portion of the pin 32, of which the shapes are likely to engage with the outer surfaces of the cylinders 42, the pin having in the lower portion, a diameter greater than the distance separating the two cylinders 42. Thus, to assemble the removable pin 32 and the tibial portion 16, recesses 52 must be placed in the extension of the cylinders 42 and to make them slide along cylinders to the desired position. At least one stop can be provided at the level of at least one cylinder to limit the translation movement of the pin with respect to the tibial portion.

The shapes of the end of the pin 32 makes it possible to obtain a removable connection with the tibial portion, by engaging with the shapes of said tibial portion.

According to a feature of the invention, the pin 32 comprises a transversal orifice 54, allowing the implementation of a screw, a cotter, a linchpin or similar, likely to pass through at least partially the lower portion of the tibia 10. This arrangement improves the anchoring of the tibial portion by ensuring a primary fixing, making it possible to limit or to avoid the use of cement and allows the immediate fixing of the cortical cap made for the passage of the pin.

In FIGS. 12 to 15, the talus portion 18 has been represented in detail.

This portion comprises a body with, in the upper portion, an articular surface 56 and, in the lower portion, means 58 for anchoring to the talus 12.

Figure 15:
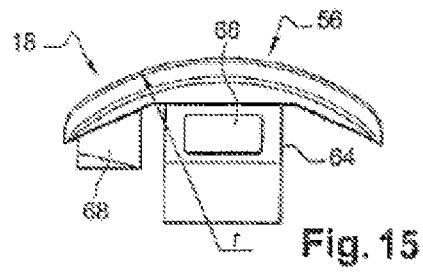
FIG. 15 is a side view along another direction of the talus portion represented in FIG. 12.

The articular surface 56 comprises, along the longitudinal direction, a profile with a bend radius r varying, for example, from 20 to 30 mm, and preferably of the order of 24 mm, as illustrated in FIG. 15.

According to an embodiment of the invention, the radius r of the articular surface 56 of the talus portion is less than the radius R, and if necessary, than the radiuses R and R', of the articular surface 24 of the tibial portion. The radius difference, and in particular, the increase of bend of the tibial slope increases the significance of the friction forces and avoids the front or rear expulsion of the pad.

Figure 14:
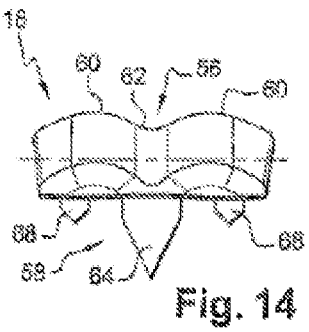
FIG. 14 is a side view along a first direction of the talus portion represented in FIG. 12.

Along the transversal direction, as illustrated in FIG. 14, the talus portion 18 comprises a profile with two waves, two convex portions 60, of radius of the order of 8 mm, separated by a concave portion 62 of radius of the order of 3 mm.

This arrangement makes it possible to obtain a better guiding of the movement of the ankle in a longitudinal vertical plane.

Preferably, the side edges of the articular surface 56 have a greater bend radius of the order of 25 to 30 mm.

According to an embodiment, the means 58 for anchoring the talus portion comprise a central stud 64, of rectangular cross-section, with a sharp distal end for a better implementation. Preferably, the central stud 64 comprises a transversal orifice 66 improving the bone recovery.

According to a feature of the invention, the anchorage means 58 preferably comprise at least one stop 68 arranged under the talus portion 18, at the level of the rear edge 70, to prevent the tilting of the talus portion 18 towards the front of the foot, as illustrated in FIG. 15.

Preferably the talus portion 18 comprises two stops 68 arranged substantially symmetrically with respect to the longitudinal median axis for a better stability.

According to an embodiment, the stops 68 have a cross-section (along a horizontal plane) with a sharp shape directed towards the front for a better immobilisation in the bone.

According to an embodiment, the tibial portion 16 and the talus portion 18 are made of any biocompatible material, for example made of highly alloyed steel, with a significant surface hardness at the level of the articular surfaces 24, 56.

In FIGS. 8 to 11, the pad 20 has been represented in detail. It comprises a body of rectangular cross-section, with in the upper portion, a first contact surface 72 likely to engage with the articular surface 24 of the tibial portion and in the lower portion, a second contact surface 74, likely to engage with the articular surface 56 of the talus portion.

Preferably, the contact surface 72 has shapes adapted to those of the articular surface 24, in particular adapted to the curved, concave surface of the articular surface 24, and comprises in the present case, a substantially spheric, concave shape of radius R and if necessary, of radiuses R and R' when the curved surface 24 has two different bend radiuses.

The contact surface 74 has shapes adapted to those of the articular surface 56, and comprises, according to a preferred embodiment, a concave bend radius r in the longitudinal plane.

Advantageously, the contact surface 74 has a surface area less than the contact surface 72, the transversal side walls 76 forming an angle of the order of 60°.

The pad 20 comprises means for facilitating its gripping and its implementation, for example in the form of at least one small conduit 78 at the level of the transversal side walls 76.

Preferably, the pad 20 is made of a material with a low friction coefficient, for example made of high-density polyethylene.

Of course, the invention is not limited to the embodiment represented and described above, but on the contrary, covers all variants, in particular concerning the shapes, the dimensions, the materials of the different elements of the prosthetic.

The invention claimed is:

1. A prosthetic ankle comprising:
   a tibial portion configured to connect to a lower end of a tibia;
   a talus portion configured to connect to a talus; and
   a pad inserted between the tibial portion and the talus portion,
   wherein the tibial portion includes an articular surface configured to engage with a first contact surface of the pad,
   wherein the talus portion includes a curved articular surface configured to engage with a second contact surface of the pad, and
   wherein the articular surface of the tibial portion is curved, concave, and comprises:
      a spheric portion extending over a portion of said articular surface, and
      a flat section forming an extension to a rear of said articular surface such that a centre of the spheric portion is not in a centre of the tibial portion along an antero-posterior axis of the tibia.

2. The prosthetic ankle according to claim 1, wherein the flat section has a width comprised between 2 and 8 mm.

3. The prosthetic ankle according to claim 1, wherein the tibial portion has a length comprised between 20 and 100 mm and a width comprised between 10 and 40 mm.

4. The prosthetic ankle according to claim 1, wherein the spheric portion of the articular surface of the tibial portion has a bend radius R comprised between 30 and 90 mm and, possibly, a second bend radius R' different from the first bend radius R comprised between 20 and 80 mm.

5. The prosthetic ankle according to claim 1, wherein the articular surface of the tibial portion is slightly inclined towards the rear of the foot.

6. The prosthetic ankle according to claim 1, wherein the articular surface of the talus portion has a bend radius r along the longitudinal axis comprised between 20 and 30 mm.

7. The prosthetic ankle according to claim 1, wherein the tibial portion comprises means for anchoring with a removable pin.

8. The prosthetic ankle according to claim 7, wherein the removable pin comprises two symmetrical recesses arranged in the lower portion of the pin, of which the shapes are configured to engage with the outer surfaces of two parallel cylinders integral with the tibial portion, the pin having, in the lower portion, a diameter greater than the distance separating the two cylinders.

9. The prosthetic ankle according to claim 7, wherein the pin comprises a transversal orifice allowing the implementation of a screw, a cotter or a linchpin configured to pass through at least partially the lower portion of the tibia.

10. The prosthetic ankle according to claim 1, wherein the talus portion comprises means for anchoring with at least one stop arranged under the talus portion, at the level of a rear edge, to prevent the tilting of the talus portion towards the front of the foot.

11. The prosthetic ankle according to claim 2, wherein the flat section has a width comprised between 4 and 6 mm.

12. The prosthetic ankle according to claim 3, wherein the tibial portion has a length comprised between 35 and 85 mm and a width comprised between 15 and 30 mm.

13. The prosthetic ankle according to claim 4, wherein the spheric portion of the articular surface of the tibial portion has a bend radius R of the order of 50 mm, and possibly, a second bend radius R' different from the first bend radius R of the order of 50 mm.

14. The prosthetic ankle according to claim 6, wherein the articular surface of the talus portion has a bend radius r along the longitudinal axis of the order of 24 mm.

* * * * *